United States Patent [19]

Dee

[11] Patent Number: 4,788,976

[45] Date of Patent: Dec. 6, 1988

[54] UNIVERSALLY ADJUSTABLE BLADE

[76] Inventor: Robert N. Dee, P.O. Box 512, Tuckahoe, N.Y. 10707

[21] Appl. No.: 62,113

[22] Filed: Jun. 12, 1987

Related U.S. Application Data

[63] Continuation-in-part of Ser. No. 831,801, Feb. 21, 1986, Pat. No. 4,672,964.

[51] Int. Cl.⁴ .............................................. A61B 17/32
[52] U.S. Cl. ....................................... 128/305; 30/321
[58] Field of Search ............... 128/305, 304, 346, 340; 30/329, 339, 321, 286, 285, 295, 87

[56] References Cited

U.S. PATENT DOCUMENTS

| 2,316,985 | 4/1943 | Niedermayer | 30/339 X |
| 3,609,864 | 10/1971 | Bassett | 30/339 X |
| 3,922,784 | 12/1975 | Prince et al. | 30/317 |
| 3,981,308 | 9/1976 | Schlein | 128/346 |

FOREIGN PATENT DOCUMENTS

| 151270 | 10/1984 | Mexico | 128/305 |
| 490072 | 6/1970 | Switzerland | 128/305 |

Primary Examiner—Michael H. Thaler
Attorney, Agent, or Firm—Murray Schaffer

[57] ABSTRACT

A single scalpel having a universally adjustable blade mounted to the scalpel handle for selected positioning through an arc of at least 90° with respect to the axis of the handle and through an arc of at least 360° about the axis of the handle thereby enabling the single scalpel to be used at any required angle and position without changing blades or scalpels.

6 Claims, 3 Drawing Sheets

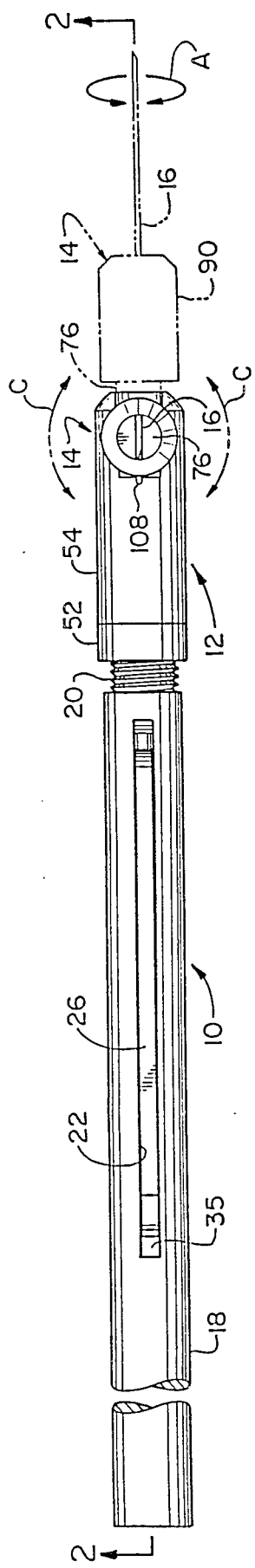
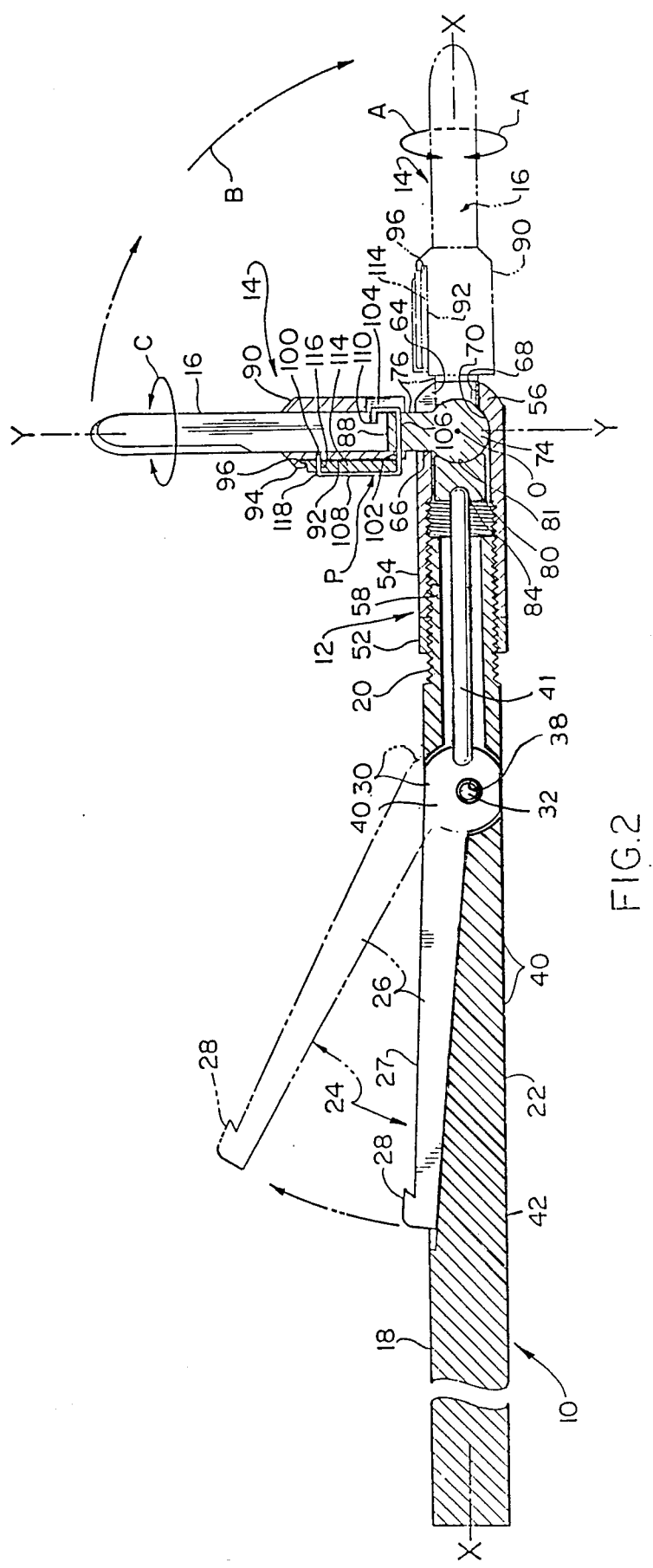
FIG.1
FIG.2

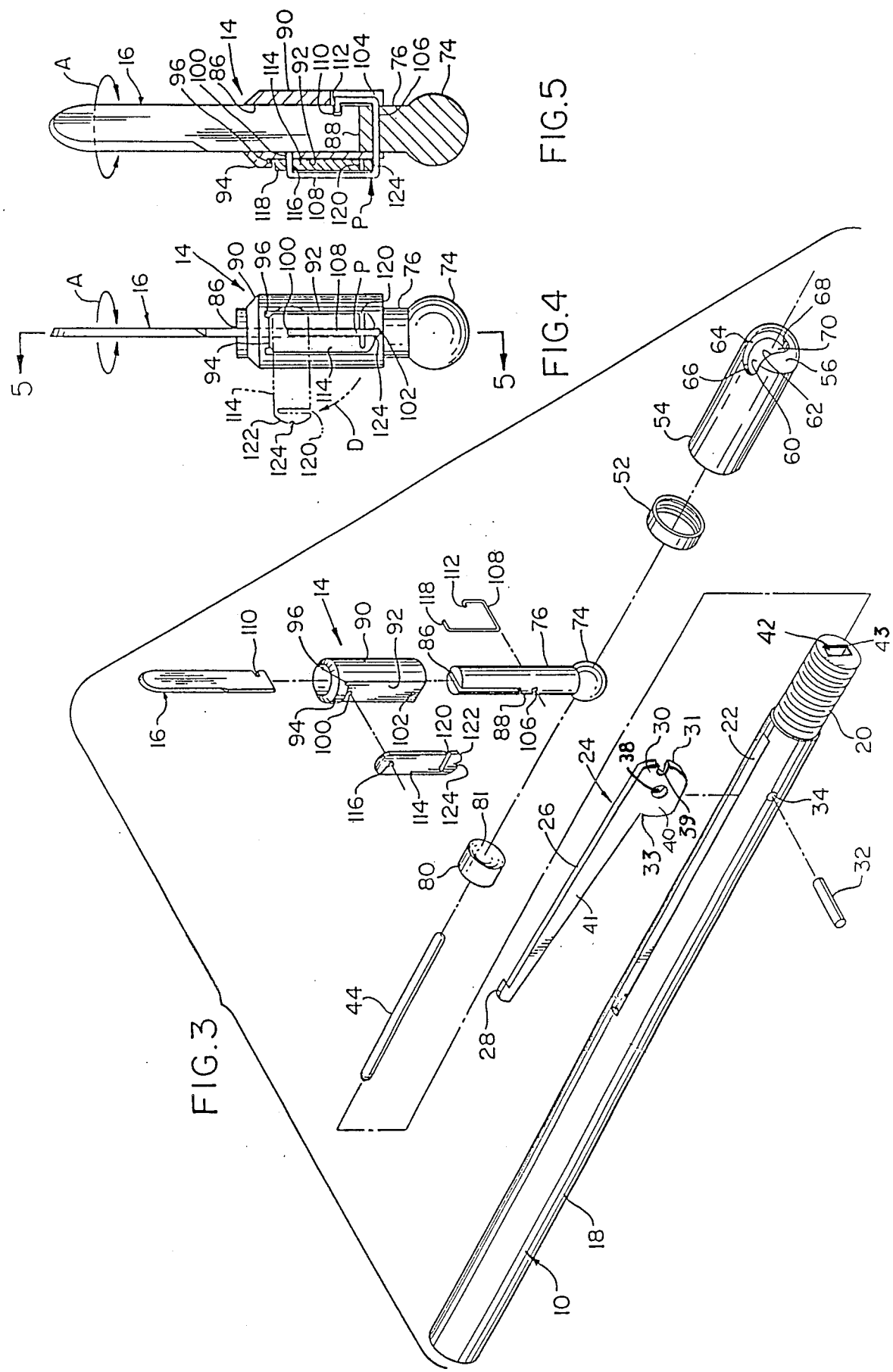

UNIVERSALLY ADJUSTABLE BLADE

RELATED APPLICATION

The present application is a continuation-in-part of Ser. No. 831,801 filed Feb. 21, 1986 now U.S. Pat. No. 4,672,964 issued June 16, 1987, of which I was a joint inventor.

BACKGROUND OF THE INVENTION

The present invention relates to a surgical scalpel and in particular to a periodontal scalpel wherein the blade is universally adjustable.

In the aforementioned patent application Ser. No. 831,801, the contents of which are incorporated herein as more fully set forth, a scalpel is provided having an elongated handle conveniently shaped in the form of a shaft, a blade located in a blade holder mounted at a distal end of the shaft, as to be universally adjustable. The blade is orientated in any one of a plurality of selected directions relative to the axis of the handle, namely, by relatively rotating the handle and blade about the axis of the shaft and/or swinging the blade in an arc subtended by the axis of the shaft and in a line perpendicular thereto, and correspondingly rotating the holder about its own axis. To effect this, the blade is held in a chuck having a ball-shaped base, which is set into a spherical socket formed in a cylindrical chuck housing, co-axially mounted at the end of the shaft. The end of chuck housing is cut in the form of a cleft defined by the axis of the shaft and perpendicular line. Mounted within the chuck housing is an operable stop member adapted to engage the ball and fixedly hold the chuck in its selected position. The stop member is operated by a crank mechanism located in the shaft-handle, which is operable and esaily manipulated by the operating hand of the surgeon during surgery via a lever extending along the surface of the shaft actuating an eccentric crank to cause the stop member to move axially within the housing into and out of engagement with the ball base of the chuck.

The present invention has as its object, the provision of an improved and simplified crank mechanism which greatly reduces the cost of manufacture and the ease by which the scalpel can be manipulated.

Another object of the present invention is the provision of a scalpel having fewer and simpler parts permitting the scalpel to be disassembled and sterilized.

It is of course, the overall object of the present invention to provide a scalpel having in addition to the above, all of the attributes and advantages found in the aforementioned parent application.

The foregoing objects, together with others, will be apparent from the following disclosure.

SUMMARY OF THE INVENTION

According to the present invention, a crank mechanism for use in the general scalpel shown in my aforementioned application comprises a crank head mounted within the handle slot between the proximal and distal ends thereof so as to be rotatably journaled about a pin extending perpendicular to the axis of the handle and psssing through the axis. The crank head has a circular surface centered about an axis parallel to the journal pin and offset therefrom to revolve in an eccentric path about an axis transverse to the central axis of the handle. A rod is interposed between the stop plate and said crank head so that when the crank head is revolved in one direction, the rod biases the head proximally to move the stop plate into the operative locking position and when the crank head is revolved in the other directrion, the rod moves distally to release said stop plate from the operative locking position. The crank lever is integrally connected to the crank head and extends radially outward from the handle when the crank head is in its inoperative position and ties flat against the handle when the crank head is in its operative position.

In practice, the crank head is provided with a notch at its distal edge to receive the rod, the notch being offset from the center of revolution of the crank head.

Full details of the present invention are set forth in the following description and illustrated in the accompanying drawings.

BRIEF DESCRIPTION OF THE DRAWINGS

In the Drawings:

FIG. 1 is a top plan view of the scalpel of the present invention;

FIG. 2 is a section taken along the diametrical plane 3—3 of FIG. 2;

FIG. 3 is an exploded isometric view of the scalpel of the present invention;

FIG. 4 is a top plan view of the chuck employed in the scalpel of the present invention;

FIG. 5 is a sectional view of the chuck taken along the plane 5—5 of FIG. 4.

DESCRIPTION OF THE INVENTION

Figure 6:
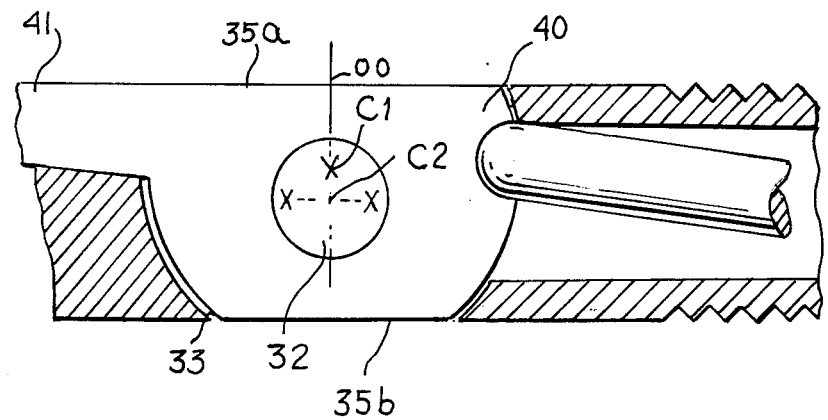
FIG. 6 is an enlarged section of the crank mechanism embodying the present invention.

As seen in FIGS. 1 and 2, the scalpel of the present invention comprises a handle 10, at the distal end of which is threaded a chuck housing 12, in which a chuck generally identified 14 is adjustably held to the chuck housing and in which a blade 16 is removably held. While the handle 10, and chuck housing 12 may have any cross-section they are here shown as being cylindrical and have a common central longitudinal axis X—X, about which the scalpel 16 is rotatable, by manual manipulation, as shown by the arrow A. The chuck 14 is arranged within the chuck housing 12 to pivot within the range of a right angle or 90h degrees as denoted by the double arrows B, while the chuck 14 and blade 16 can rotate as a unit clockwise and counter-clockwise about the axis Y—Y of the blade in the directions denoted by the double arrows C.

The handle 10 preferably comprises a solid shaft 18 made of surgical steel that may be knurled or sculptured (not shown) on its exterior surface as may be desired to facilitate its easy grasping by the surgeon or dentist. The outer surface at the forward or distal end of the shaft-handle is threaded as at 20 to provide a removable seat for the chuck housing 12. A slot 22 is provided in the shaft 18 to the rear of the threaded distal end. The slot 22, has parallel sides which pass diametrically through the shaft 18 and has inserted therein a plate-like locking crank, generally denoted by the numeral 24.

The locking crank 24 comprises a lever arm portion 26 extending proximally, terminating in a raised finger ridge 28 for easy manipulation and has a depending eccentric crank head 30 at its distal end. The locking crank 24 is held within the slot 22 by a retaining pin 32 removably inserted through a bore 34 extending diametrically through the shaft 18 perpendicular to the plane of the sidewalls of the slot 22. A shallow elongated groove is cut in the shaft 18, extending rearwardly of the slot 22, so that the lever 26 seats therein. The groove provides a rest stop which maintains the outer exposed surface 27 of the lever 26 in a generally parallel position to the axis of shaft 18 and the finger ridge 28 above the surface of the slot of the shaft 18. This is referred to hereinafter as the locking position.

As seen in detail in FIG. 3, the disk-like crank head 30 has a forward edge 31 and a rear edge 33 being arcuate sections of a common circle illustrated in the dotted lines having a center C1 which is offset in the plane of the slot 22 about the horizontal axis X—X. The remaining portions of the disk-like head 30 along the common circle are cut away chordally at 35a and 35b so as to conform to the exterior surface of the shaft 18. The slot 22 conforms in shape to the disk-like crank head 30 having an arcuate wall 36 at its forward edge and an arcuate wall 37 at its rear edge.

The crank head 30 has a journalling hole 38 and is rotatably mounted about the centering pin 32 having a center C2 lying in the axis X—X below the center C1 of crank head 30. The line 0—0 on which the two centers C1 and C2 lie is perpendicular to the axis X—X and is centered in plane between the sidewalls of the slot 22. Thus, the crank head 30 is eccentric to the center C2.

A shallow recesses 39 is formed in the forward edge 31 of the crank head 30. The recess 39 receives and retains the rear end 40 of a locking rod 41 which passes freely through an axially extending slot 42 form on the diametrically opposed surfaces of the inner wall of the bore 43 of the distal portion of the shaft 18. The slot 42 is relatively enlarged to permit the rod 41 freedom of movement therein, in the plane of the slot 22

The recess 39, is formed on the periphery in radial alignment with the center C1 of the crank head 30, so that when the crank 26 is set in the locking position, (moved counter-clockwise), as earlier defined, the end 40 will lie above the axis X—X. Because of the eccentricity of the edge 31 with respect to the center C2 of the pin 32, the recess 39 is moved linearly outward in the direction of the axis X—X so that the locking bar 41 is pushed outwardly toward the distal end. On the other hand, when the lever 26 is raised (clockwise) the head 30 rotates downwardly moving the recess 39 below the axis X—X so that, because of the same eccentricity, the recess 39 is radially closer to the center C2 of the pin 38. In this manner, pressure on the locking bar 41 is relaxed.

Figure 7:
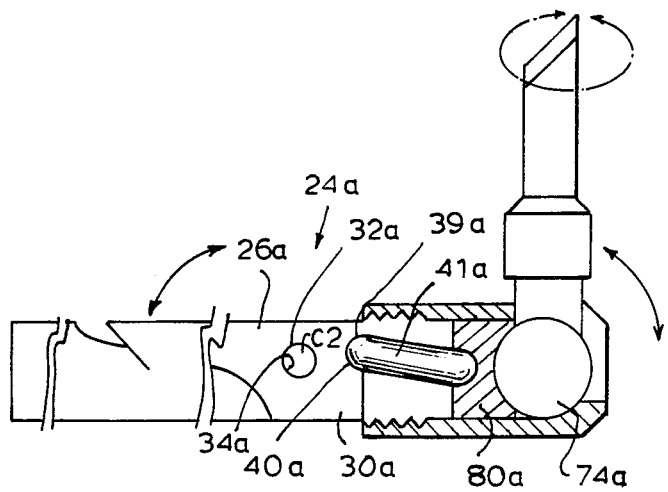
FIG. 7 is a view similar to FIG. 6 showing a second embodiment of the present invention.

In a second embodiment illustrated in FIG. 7, the lever 26a and head 30a is shaped somewhat differently, although the exact shape, it is not critical. The head 30a is journalled about a removable pin 32a which passes through a bore 34a having a center C2 offset above the central axis X—X. The recess 39a on the periphery of the head 30a is aligned with the axis of the pin 32a of slightly above it so that the line drawn between them is parallel or at a slight angle upwardly from the axis X—X. This provides an eccentric mounting for the lever assembly 24a. In this manner, when the lever 26a is placed in the locking position, as shown (rotated counter clockwise) the end 40a of the locking bar 41a moves upwardly causing the locking bar to compress the locking plate 80a against the chuck ball 74a. On the other hand, when the lever 26a is raised, the locking bar 41a moves downwardly below the axis X—X, increasing the distance between the recess 39a and the locking plate, thus relaxing pressure on the locking bar 41a and releasing the blade chuck for adjustment.

Turning now to FIGS. 2 and 3, the chuck housing 12 for rotatably mounting the blade 16 to the handle is held in its desired position on the distal end of the shank 18 by a jamb nut 52 and comprises an extended hollow sleeve 54 substantially closed at its forward end by a spherical wall 56. The sleeve 54 is provided with an internally threaded rear end 58 adapted to screw over the forward threaded end 20 of the shaft-handle 18 to any desired angle of at least 360 degrees about an axis extending through the length of the handle 10 and to be locked in such position of adjustment by the lock or jamb nut 52. Both the shaft-handle 18 and the inner surface of the sleeve 54 of the chuck housing 12 may be provided with appropriate shoulders or retaining washers (not shown) against which rotation of the sleeve 54 is limited and locked and which enables the sleeve 54 to be held in fixed place during use by the surgeon, in lieu of using the jamb or lock nut 52.

A cleft or cut-away opening 60 is formed at the distal end of the chuck housing sleeve 54 by removing a sector of the enclosing spherical wall 56. The cleft 60 is defind by the axially or longitudinally extending parallel walls 62 and 64 and semi-round transverse rear and forward walls 66 and 68, respectively. In this manner, the defines of the cleft 60 provide, in cross-section (FIG. 2), a substantially rectangular opening in the housing sleeve 54. The interior surface of the housing sleeve 54 as well as the adjacent partial sections of the cylindrical wall of the sleeve 54 are concavedly formed to provide a spherical cup 70 into which the base 74 of the chuck 14 seats as seen in FIG. 2.

The chuck 14 as seen in detail in FIGS. 4 and 5 comprises the spherical base 74 and an extending cylindrical shank 76. In assembly, as seen in FIG. 2 the base 74 fits slidably within the cup 70 and the cylindrical shank 76 extends outwardly through the cleft 60. The cup 70, and the base 74 are dimensioned to have the same center "0" which passes through the axis "X" of the shaft 18 so that the ball 74 and cup 70 provide a smooth working joing that has universal movement within the cup 70. Similarly, the diameter of the chuck shank 76 and the distance between the parallel walls 62 and 64 are also dimensioned to allow free movement of the shank 76 between the relativel spaced end walls 66 and 68 that also includes movement relative to the parallel walls 62 and 64.

In this configuration, the chuck shank 76 can be made to simultaneously swing through an arc of at least ninety (90) degrees between the rear end wall 6 and the forward end wall 66 and the forward end wall 68 through the angle shown by the double arrow B, and rotate endlessly through an arc of at least 360° about the axis Y—Y as shown by double arrows C. The arc B can be increased or decreased by correspondingly changing the relative space between the limiting walls 66 and 68. Obviously, if the relative space is greater, the angle B will be greater.

To secure the chuck 14 in any one of its infinite positions, a locking plate 80 (FIG. 2) is located within the housing sleeve 54 in sliding abuttment with the ball shaped base 74 of the chuck 14. The locking plate 80 has a spherical frontal face 81 and is provided on its rear surface 82 with a blind bore 84 into which forward end of the front locking rod 44 is fixedly seated. When the forward locking rod 44 is moved forwardly (to the right as viewed in the drawing) by placing the crank 24 in the locking position, the plate 80 is pushed forward placing its front face 81 into secure abutment against the ball 74, thus forcing the ball 74 simultaneously against the surface of spherical cup 72 and thereby securely seating the ball 74 against any further movement. Adjustment of the chuck 14 is made merely by placing the lever 26 into the release position thereby removing the tension on rod 44. This further releases the locking plate 80 permitting it and ball 74 to slide relatively to each other.

The surface of the ball-shaped base 74 of the chuck 14 and/or the spherical face 81 of the locking plate 80 might be sculptured or provided with knurls, ratchet teeth or the like to insure secure locking of the parts. The locking position is maintained during actual use of the scalpel, notwithstanding severe pressure placed thereon by the doctor, to the biasing, resulting from the positioning of the rear and front locking levers 40 and 44 as well as the fact that the lever 26 is normally maintained depressed by the surgeons hand.

As seen in FIG. 3, to accommodate the blade 16, the cylindrical shaft 76 of the chuck 14 is bifurcated at the end opposite the ball shaped base 74 to provide an open ended axially slot 86 having an inner wall 88. As seen in FIGS. 4 and 5, the blade 16 is held in place in the slot 86 of the cylindrical shank 76 by a retaining ring 90 which is generally cylindrical on its inner surface and which has an ID to fit closely about the shank 76. The ring 90 is provided with a chordal land 92 on its outer surface and is left, when formed, with a shoulder 94 at the front edge of the land 92. The shoulder 94 is provided with a tab 96 which overlaps the land 92 and forms a recess 98 therewith.

The retaining ring 90 is provided with a hole 100 at the front end and a hole 102 at its rear end which passes through the land 92 in alignment along the longitudinal center line of the land 92. On the diametrically opposite side of the ring 90 from the rear hole 102 there is formed a slot 104 extending inwardly from the rear edge of the ring 90, for a short distance. The cylindrical shank 76 of the chuck 14 is provided with a diametrical through-bore 106 which extends just behind the inner wall 88 of the slot 86 into which the blade 16 is inserted.

A multi-angular spring 108 passes about the ring 90 extending through the bore 106 in the chuck shank 76 from the front hole 100 through the rear hold 102 into the axial slot 104 of the ring 90. The blade 16, is itself formed with a notch 110 along its lower edge 12 at point which opens to the slot 104 in the ring 90 so that the tail end 112 of the spring 108 will lodge securely in the notch 110. The spring 108 is made of heavy gauge piano wire which is capable of being bent into shape in insertion into the ring 90, in situ, and yet retain its highly resilient nature after bending. Once the spring 108 is bent into place, the blade may be released from the spring 108, by depressing the rear end of the spring 108 at the point indicated by the numeral P, FIG. 5 so that the short tail end 112 of the spring 108 moves downwardly through the slot 104 and out of the notch 110 in the blade 16. This frees the blade 16 for removal through the front end of the slot 86 and the retaining ring 90. The blade 16 can also be easily replace by inserting a similar blade through the ring 90 into the chuck slot 88 after depressing the retaining spring 108 which when left free will again engage the notch 110 and secure the blade in place.

In order to prevent the retaining spring 108 from being unnecessarily depressed while the scalpel 10 is being handled, and thereby inadvertently releasing the blade 16, a slide member 114 is inserted between the spring 108 and the surface of the land 92 of the retaining ring 90. The slide member 114 has a hole 116 at its forward end through which the head end 118, of the spring 108, passes into the front hole 100 of the ring 90, while the slide plate 114 engages beneath the overlapping tab 96. The slide plate 114 is permitted to be swung about the axis of spring head end 118 parallel to the surface of the land 92 to one side of the spring 108 as shown by the double arrows D in FIG. 4. The slide plate 114 is provided with a slit 120 extending transversely to the longitudinal axis of the plate 114, which slit defines a resilient finger 122 at the rear most edge of which is a notch 124 which is adapted to engage the spring 108 and hook therewith to hold the slide in place beneath the longitudinal section of the spring 108. With the plate 114 secured in this position, the spring 108 cannot be depressed.

It is thus readily apparent from the foregoing description that the earlier enumerated objects have been met and that a scalpel is provided in which the blade 16 has a universal movement in the arc defined by the arrows B, between a position in line with the axis "X" of the handle and 90 degrees offset from the axis "X" of the handle while the cutting edge of the blade may be rotated clockwise and counter clockwise (arrow C) about is own axis Y—Y through an arc of at least 360 degrees and while the surgeon rotates the scalpel about the axis "X" (arrows A). This enables the surgeon to situate the cutting edge of the blade in any desired position with respect to the surface to be surgically treated without having to remove the blade from its holder and without having to change blades in the holder. The same surgical blade may be used regardless of the angular position in which the cutting surface must be treated.

Locking of the blade 16 in its selected position of operation is further insured by the mechanism described, which also permits the release of the blade enabling it to be moved to another selected position of usage, by simple upward movement at the proximal end of the lever 26. Even a short upward movement will release the pressure of the plate 80 against the ball 74 allowing the blade to be easily moved.

Another feature of the invention is apparent from the mechanism utilized to retain the blade in the rotating chuck mechanism. Not only does the combination of ring 90 and wire spring 108 permit quick and easy removal of the blade for substitution with another blade, but permits the use of blades which do not have any special configuration. That is, the blades need only be flat and have a single retaining notch (notch 110) for cooperating with the retaining spring.

The foregoing disclosure sets forth several forms and embodiments. Changes, additional embodiments, and modifications will also be apparent to those skilled in this art. The disclosure, therefore, is to be taken as illustrative and not limiting of the invention.

What is claimed is:

1. A scalpel comprising an elongated cylindrical handle closed at its proximal end and having a hollow sleeve portion formed with a spherical socket and cleft at its distal end adapted to receive a chuck in which a blade is fixedly secured, said chuck including a spherical base slideably seated in said socket for rotation of said chuck in an arc of at least 360 degrees therein and a shank extending through said cleft for swinging said chuck in an arc of at least 90 degrees, means for releasably locking said chuck in a selected position of rotation and swing comprising a stop plate slidable axially within the sleeve portion in opposition to the spherical base of said chuck and an over-the-center crank mechanism to alternately effect proximal movement of said stop plate into an inoperative position free of said spherical base thereby permitting rotation of said chuck or distal movement of said stop plate into an operative position pressed against said spherical base to lock said chuck against rotation, said crank mechanism being located in a slot having parallel sidewalls and comprising a crank head mounted within said slot between the proximal and distal ends thereof, said crank head being rotatably journaled about a pin having a transverse extending perpendicular to the center axis of said handle and passing through the center axis of said handle, aid crank head having a circular surface centered about an offset axis parallel to the transverse axis of said pin and offset therefrom to revolve in an eccentric path about said transverse axis, a rod interposed between said stop plate and said crank head so that when said crank head is revolved in one direction, said rod biases said head to move said stop plate into the operative locking position and when said crank head is revolved in the other direction said rod moves to release said stop plate from the operative locking position, and a lever integrally connected to said crank head and extending radially outward from said handle when said crank head is in its inoperative position and lying flat against said handle when said crank head is in its operative position.

2. The scalpel according to claim 1, wherein said chuck shank is provided with an axial slot in which said blade is received, a collar surrounding said chuck shank to encompass said blade, and means for releasably securing said collar and the blade to said chuck shank.

3. The scalpel according to claim 2, wherein said means for securing said collar and said blade comprises a wire spring passing through said collar, the chuck shank and at least part of said blade, said spring being releasably from the blade to permit removal of the blade from said slot without disengagement from said collar and chuck shank.

4. The scalpel according to claim 1, wherein said handle is provided with a diametric slot into which said crank head is located.

5. The scalpel according to claim 4 wherein said crank head is provided with a notch at its distal edge to receive said rod, said notch being offset from the offset axis of said crank head.

6. The scalpel according to claim 1, wherein said sleeve portion comprises a separable hollow tubular member threadedly connected at its distal end to said handle, said sleeve being thereby capable of adjusting the distance of said socket to said crank head and the pressure of said first rod on said stop plate.

* * * * *